United States Patent [19]

Larach et al.

[11] 4,233,989
[45] Nov. 18, 1980

[54] ECHOCARDIOGRAPHIC APPARATUS FOR MYOCARDIAL DISEASE DIAGNOSIS BY A-WAVE QUANTIFICATION

[75] Inventors: Simon Larach; David H. R. Vilkomerson, both of Princeton, N.J.

[73] Assignee: RCA Corporation, New York, N.Y.

[21] Appl. No.: 973,456

[22] Filed: Dec. 26, 1978

[51] Int. Cl.³ .................................................. A61B 10/00
[52] U.S. Cl. .................................... 128/661; 73/612
[58] Field of Search ................................ 73/599–600, 73/609–610, 612, 648; 128/660–663, 599–600, 609–610, 612, 646

[56] References Cited

U.S. PATENT DOCUMENTS

| | | | |
|---|---|---|---|
| 3,194,057 | 7/1965 | Richard | 73/599 |
| 3,427,867 | 2/1969 | Nute et al. | 73/599 |
| 3,624,712 | 11/1971 | Weighort | 73/610 |
| 3,673,325 | 6/1972 | Uphoff | 73/610 |
| 3,802,253 | 4/1974 | Lee | 128/660 |
| 4,011,750 | 3/1977 | Robinson | 73/602 |
| 4,057,049 | 11/1977 | Hill | 28/660 |

*Primary Examiner*—Robert W. Michell
*Assistant Examiner*—Francis J. Jaworski
*Attorney, Agent, or Firm*—Samuel Cohen; George J. Seligsohn

[57] ABSTRACT

A-wave quantification indicator automatically measures the difference in amplitude between the peak of the E-wave portion of an ultrasonically derived M-wave CRT display and the peak of the A wave portion of the M-wave. This difference in amplitude, which distinguishes myocardial-disease and hyperkinetic syndrome subjects from normal subjects, is alphanumerically displayed in quantitative and/or qualitative terms.

6 Claims, 6 Drawing Figures

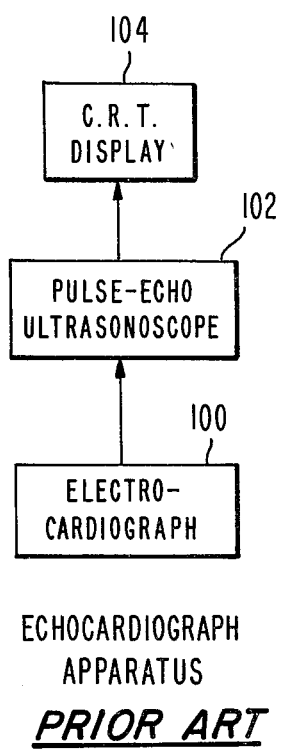
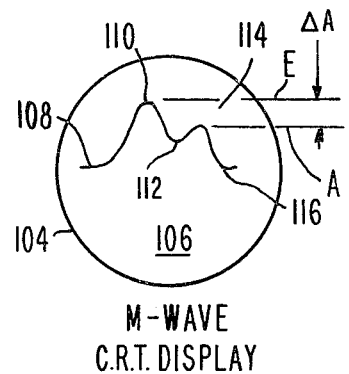
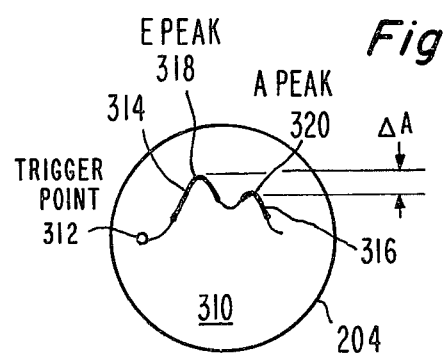
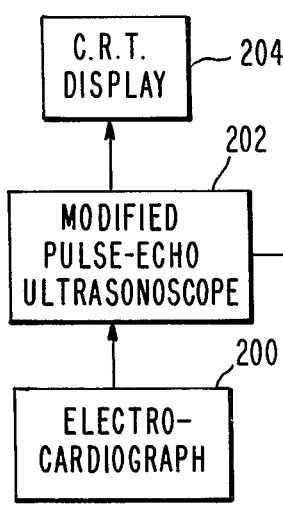
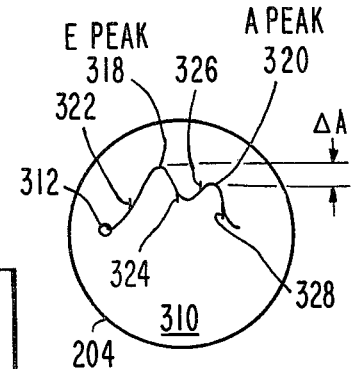

ECHOCARDIOGRAPHIC APPARATUS FOR MYOCARDIAL DISEASE DIAGNOSIS BY A-WAVE QUANTIFICATION

This invention relates to improvements in echocardiograph apparatus and, more particularly, to apparatus for the rapid clinical echocardiographic diagnosis of myocardial disease by A-wave quantification.

Echocardiography is a known non-invasive diagnostic technique for evaluating the left ventricular function of the heart. Specifically, the insonification of the beating heart with a pulse of ultrasonic wave energy gives rise to an ultrasonic echo that has an intensity which varies in time in accordance with characteristics of the beating heart. All or only a selected portion of detected signals of such echoes from each of successive heart beats comprises a waveform which may be displayed on a cathode ray tube (CRT) display (e.g. oscilliscope). Such a displayed waveform constitutes an echocardiogram having certain characteristics which correlate with heart function (in a manner somewhat analogous to that of an electrocardiogram).

One particular known echocardiogram waveform is the so-called M-wave. The M-wave is composed of a first-occurring portion followed by a second occurring portion. The first-ocurring portion, known as the E-wave, consists of a signal amplitude which rises with time from a given level to a first (higher) peak and then falls to the bottom of a valley. During the second-occurring portion, known as the A-wave, the signal amplitude rises from the bottom of this valley to a second (lower) peak and then falls back towards the given level, which is at a value below that of the bottom of the valley.

It has been shown that the M-wave, and particularly the A-wave portion thereof, is related to the algebraic sum of the overall heart motion and the individual motion of the leaflet of the mitral valve of the heart.

One of the two present inventors (Larach) has made respective echocardiographic investigations of a group of normal subjects, a group of subjects who were suffering from hyperkinetic heart syndrome and a group of subjects who were suffering from either primary myocardial disease or coronary artery disease with myocardial ischemia, which show that there is a very high correlation between the difference in height between the first (higher) and second (lower) peaks of the M-wave and heart disease. Specifically, the difference in height between these two peaks for normal subjects was in a range of 9.7±0.8 mm. However, the difference between these two peaks for hyperkinetic patients was significantly higher, being in the range 14.1±1.3 mm. On the other hand, patients with cardiomyopathy, coronary heart disease or primary myocardial disease exhibited a difference between these two peaks in the range of 4.2±0.9 mm, which is significantly lower than that of normal subjects.

The present invention is directed to improved echocardiograph apparatus which, quickly and accurately, measures automatically the difference between the two peaks of the M-wave and then qualitatively and/or quantitatively indicates the results of this measurement. Such improved apparatus is particularly useful for clinical screening and diagnosis of any of the above-described myocardial or hyperkinetic diseases.

In the drawings:

FIG. 1 is a block diagram of prior art echocardiograph apparatus;

FIG. 1a illustrates the display of an M-wave on the CRT display of the prior art echocardiogram apparatus;

FIG. 2 is a block diagram of improved echocardiograph apparatus incorporating the present invention;

Figure 3:
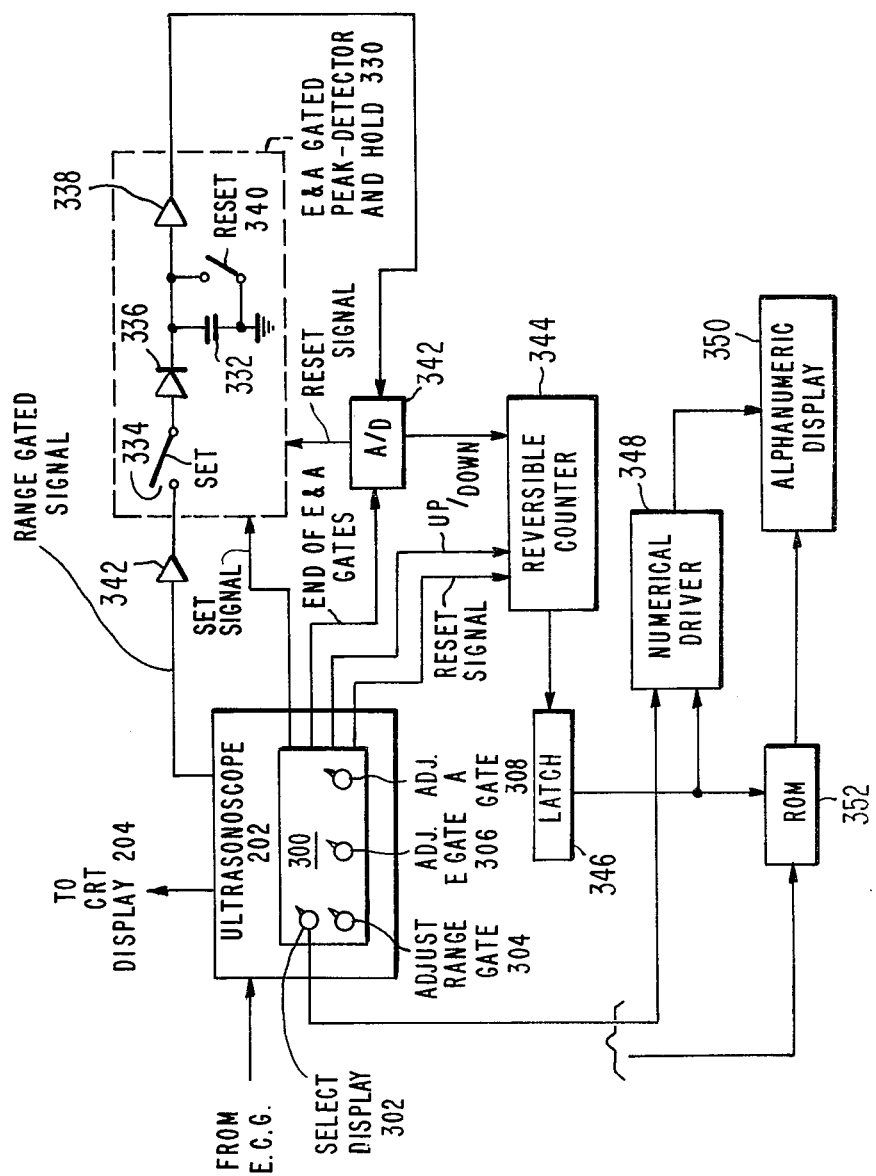
FIG. 3 is a block diagram of an embodiment of the A-wave quantification indicator of FIG. 2, and FIGS. 3a and 3b, respectively, illustrate alternate modifications of the M-wave CRT display of FIG. 1a, which may be obtained with the improved echocardiograph apparatus of FIG. 2.

As shown in FIG. 1, prior art echocardiographic apparatus is comprised of a conventional electrocardiograph 100, a commercially available pulse-echo ultrasonoscope (e.g. Ekoline model 20A ultrasonoscope) 102, and an oscilloscope CRT display 104. For echocardiographic purposes, the only function of electrocardiograph 100 is to apply to pulse-echo ultrasonoscope 102 trigger pulses which are synchronized with the heartbeat of the subject being examined. Pulse-echo ultrasonoscope 102 includes a movable electro-acoustic transducer (e.g. a non-focused transducer 12 mm in diameter) which is intermittently energized by an ultrasonic frequency (UF) pulse. The occurrence of each UF pulse is synchronized with each heartbeat of the subject being examined by the trigger pulse applied to pulse-echo ultrasonoscope 102 from electrocardiograph 100. The frequency of each UF pulse is at a predetermined value (e.g. 2.25 MHz). In response to the application thereto of each UF pulse, the transducer of pulse-echo ultrasonoscope 102 launches a pulsed beam of ultrasonic wave energy which is propagated at a predetermined velocity through the insonified tissue of the subject being examined. The insonified tissue reflects some of the ultrasonic wave energy, which as an echo, returns to and is detected by the transducer. The detected echo signal, as a function of time, corresponds with the depth of the insonified tissue, in accordance with the velocity of propagation of the ultrasonic wave energy. Since the depth of the insonified tissue of interest may vary, pulse-echo ultrasonoscope 102 is usually equipped with an adjustable range gate for forwarding to CRT display 104 only that portion of the detected signal which corresponds to the insonified tissue of interest. The range gated detected signal forwarded to CRT display 104 may be coupled to the vertical deflection plates of the CRT, while a horizontal sweep of the CRT may be initiated substantially at the beginning of the occurrence of each range gated detected signal. This results in CRT display 104 displaying a waveform shape which is related to the ultrasonic reflecting characteristics of the insonified tissue of interest of the subject being examined.

Prior art echocardiograph apparatus, of the type shown in FIG. 1, was employed by Larach in the clinical echocardiograph investigation of myocardial disease, discussed above. This investigation leads to the conclusion that the amount of difference between the two peaks of an M-wave echocardiogram distinguished among normal subjects, subjects suffering from hyperkinetic syndrome, and subjects suffering from any of one or more of certain myocardial diseases.

Specifically, Larach, in making this investigation, used a non-focused transducer, 12 mm in diameter, of an Ekoline 20A ultrasonoscope operating at 2.25 MHz, which was placed at the third or fourth intercostal space at the left sternal border, and aimed substantially perpendicular to the chest wall, to record the mitral valve echocardiogram of each subject, who was in a recumbent position. An adjustable range gate was adjusted in accordance with the depth of the mitral valve of the heart of the subject, with respect to the position of the transducer, to produce an M-wave display on the face of CRT display 104.

Referring to FIG. 1a, there is shown a typical display of the waveform of the M-wave on the face of CRT display 104. The instantaneous amplitude of M-wave 106, from left-to-right rises from a low level 108 to a first peak 110, then falls to a minimum 112 (which is substantially higher than level 108), then rises again to second peak 114 (which is substantially lower than first peak 110), and then finally falls to point 116 (which is substantially below minimum point 112). Thus, minimum point 112 is located at the bottom of a valley situated between first peak 110 and second peak 114. The first waveform portion of M-wave 106, consisting of the rise from level 108 to first peak 110 and the fall to minimum point 112 at the bottom of the valley is known in the art as the E-wave and the remaining waveform portion of M-wave 106, consisting of the rise from the minimum point 112 to the second peak 114 and the fall to point 116, is known in the art as the A-wave. Further, first peak 110 is defined as the E peak and second peak 114 is defined as the A peak. As shown in FIG. 1a, the difference in amplitude between the E peak (at point 110) and the A peak (at point 114) is designated $\Delta A$, since the E peak is equal to the A peak plus $\Delta A$. It is the size of the displacement $\Delta A$ that has been found by Larach, with high correlation, to discriminate among normal subjects (those found to have $\Delta A$ values in the range 9.7±0.8 mm), hyperkinetic heart syndrome subjects (those found to have a $\Delta A$ value in the range of 14.1±1.3 mm), and subjects with cardiomyopathy, coronory heart disease, and primary myocardial disease (those with a $\Delta A$ value in the range of 4.2±0.9 mm).

Referring now to FIG. 2, there is shown electrocardiograph 200, modified pulse-echo ultrasonoscope 202 (shown in somewhat more detail in FIG. 3), CRT display 204, and A-wave quantification indicator 206 (shown in detail in FIG. 3). Electrocardiograph 200 and CRT display 204, in all material respects, are substantially identical to electrocardiograph 100 and CRT display 104 of FIG. 1. Except for the minor modifications described in connection with FIG. 3, ultrasonoscope 202, in all material respects, is substantially identical to ultrasonoscope 102 of FIG. 1.

Referring to FIG. 3, ultrasonoscope 202 includes a control panel 300 equipped with a select display switch 302, a potentiometer for adjusting range gate 304, a potentiometer for adjusting E gate 306, and a potentiometer for adjusting A gate 308.

Each of gates 304, 306, and 308 may include an individual voltage-controlled monostable multivibrator, which time delays a trigger pulse applied thereto by an adjustable amount which is determined in accordance with the setting of the potentiometer of that individual gate.

A trigger pulse is applied as an input to the monostable multivibrator of adjustable range gate 304 in time coincidence with the occurrence with each UF pulse applied to the transducer. Each delayed trigger pulse generated by the monostable multivibrator of adjustable range gate 304 initiates the generation of a range gate pulse having a duration at least as long as that of an M-wave. Further, each delayed trigger pulse of the monostable multivibrator of adjustable range gate 304 is applied as a trigger input of the monostable multivibrator of adjustable E gate 306. The maximum time delay provided by adjustable E gate 306 need be no greater than the duration of an E-wave. The delayed trigger from adjustable E gate 306 may initiate an E gate pulse having a fixed duration substantially smaller than that of an E-wave. Alternatively, either the delayed trigger or the lagging edge of the E gate pulse of adjustable E gate 306 may be applied as a trigger input to the monostable multivibrator of adjustable A gate 308. The sum of the maximum time delays provided by adjustable E gate 306 and adjustable A gate 308 need never be more than the duration of the M-wave. The delayed trigger for the monostable multivibrator of adjustable A gate 308 may initiate an A gate pulse having a fixed duration which is substantially smaller than the A wave.

Regardless of the particular structure of adjustable range gate 304, adjustable E gate 306 and adjustable A 308, these gates are operated to provide the type of display of an M-wave on CRT display 204 shown in FIG. 3a or, alternatively, the type of display shown in FIG. 3b. All those detected echo signals which occur during the range gate pulse are forwarded to the vertical deflection terminals of CRT display 204. In the case of FIG. 3a, both the E gate pulse and the A gate pulse are also applied to the intensity-control electrode of CRT display 204 to thereby intensify the electron beam thereof during the occurrence of each of the E and A gate pulses. In case of FIG. 3a, the E and A gate pulse, after being passed through a differentiating circuit, are summed with the range gated detected signal.

During operation, first the time delay of range gate 304 is adjusted until the entire M-wave falls within the range gate and, therefore, is displayed on the face of CRT display 204, as shown in FIGS. 3a and 3b. Trigger point 312, situated at the beginning of M-wave 310, corresponds with the coincident occurrence of the delayed trigger of range gate 304 and the trigger input to E gate 306. In FIG. 3a, this results in a first portion 314 and a second portion 316 of the M-wave trace 310 being intensified. The relative position of intensified portion 314 on M-wave 310 depends on the delay setting of adjustable E gate 306. Similarly, the relative position of intensified portion 316 depends on the time delay setting of adjustable A gate 308. E gate 306 is adjusted so that intensified portion 314 includes E peak 318 and A gate 308 is adjusted so that intensified portion 316 includes A peak 320.

In FIG. 3b, positive-going pip 322 and negative-going pip 324 (corresponding respectively to the leading and lagging edges of the E gate pulse) are substituted for intensified portion 314. Similarly, positive-going pip 326 and negative-going pip 328 (corresponding respectively to the leading and lagging edges of the A pulse) are substituted for intensified portion 316. The operation of the adjustable gates to produce the display shown in FIG. 3b (with E peak 318 included between pips 322 and 324 and A peak 320 included between pips 326 and 328) is identical to that described in connection with FIG. 3a.

The structure shown in FIG. 3, other than ultrasonoscope 202, comprises A-wave quantification indicator 206. Specifically, indicator 206 includes E and A gated peak-detector and hold circuit 330, which is composed of storage capacitance 332, a charging circuit for storage capacitance 332 including normally-open set switch 334 and diode 366, an output circuit for storage capacitance 332 comprising high-input impedance amplifier 338 and a discharge circuit for storage capacitance 332 comprising normally-open reset switch 340. Although switches 334 and 340 are schematically shown in FIG. 3 as mechanical switches, it should be understood that in practice they would be electronic switches. Normally-open set switch 334 is closed only during the presence of either the E or A gate pulse, which are applied as a set signal to peak-detector and hold circuit 330.

Therefore, during the presence of the E gate pulse, the range-gated signal from ultrasonoscope 202 is applied through buffer amplifier 342, closed switch 334 and diode 336 to storage capacitance 332. This results in storage capacitance 332 being charged to a first voltage which is proportional to E peak 318. Storage capacitance 332 holds this first voltage charge so long as reset switch 340 remains open, since output amplifier 338 has a very high input impedance and diode 336 has a very high reverse impedance.

The output from peak-detector and hold circuit 330 is applied as an input to analog-to-digital converter 342. Analog-to-digital converter (A/D) 342 is a device, known in the art, that generates a serial train of pulses, the number of pulses in the train being determined by the magnitude of the input signal to converter 342. This may be accomplished by integrating the pulses of a serial stream applied to the converter output until the integrated magnitude corresponds with the magnitude of the analog input and then terminating the stream. In any event, reversible counter 344, which initially is in its count UP condition, counts the number of pulses in the pulse train applied thereto from A/D converter 342. At the end of the E gate, control 300 applies a control signal to A/D converter 342, which results in a reset signal being applied to peak-detector and hold 330. This reset signal closes reset switch 340, thereby discharging storage capacitance 332. Further, control 300 now applies an UP/DOWN control signal to reversible counter 344, placing counter 344 in its DOWN count condition. Nothing further happens until the occurrence of the A gate, when set switch 334 is again closed. The operation of peak-detector and hold circuit 330 and A/D 342 during the A gate is identical that described above during the occurrence of the E gate. However, during the A gate, reversible counter 344 counts down in response to the pulse train applied thereto from A/D converter 342.

At the end of the A gate, reset switch 340 is again closed to discharge storage capacitance 332, and reversible counter 344 is switched to its UP count condition. For a single heartbeat, the count stored in reversible counter 344 at the end of the A wave for that single heartbeat is proportional to the difference $\Delta A$ between E peak 318 and A peak 320 for that particular single heartbeat. The count in reversible counter 344, at the end of each single heartbeat, may be loaded into latch 346. However, preferably, reversible counter 344 is operated through a predetermined number (e.g. 10) successive complete heartbeats before the count stored in reversible counter 344 is loaded into latch 346. In this case, the count loaded into latch 346 is proportional to the average of many heartbeats. The reason this is preferable is that the value of $\Delta A$ may vary slightly from one heartbeat to the next, so that greater accuracy is obtained by employing many successive complete heartbeats.

Select display switch 302 is used to control the aliphanumeric display of the information defined by the count stored in latch 346 in quantitative form, qualitative form or both quantitative and qualitative form. Specifically, in a first switch position of select display 302, numerical driver 348 is enabled to effect the display on alphanumerical display 340 of the numerical value of $\Delta A$ in units of displacement (such as millimeters), in accordance with the count stored in latch 346. Numerical driver 348 may include a divider and/or a digital arithmetic element required to convert the counts stored in latch 346 into the appropriate signals required by alphanumeric display 350 to effect the quantitative display of $\Delta A$.

In a second position of select display switch 302, read-only memory (ROM) 352 is enabled. ROM 352, when addressed from latch 346 by a count within a first given range, translates this first address into those certain alphabetic signals for alphanumeric display 350, which result in alphanumeric display 350 displaying "NORMAL" or alternatively, an abbreviation thereof, such as "NOR". However, when ROM 352 is addressed from latch 346 with a count within a second given range that is higher than the first given range, ROM 352 translates this second address into the appropriate alphabetic signals for alphanumeric display 350 which results in alphanumeric display 350 displaying the work "HYPERKINETIC" or alternatively, an abbreviation thereof, such as "HYP". In response to ROM 352 being addressed from latch 346 with a count within a third given range lower than the first given range, ROM 352 translates this third address into alphabetic signals for alphanumeric display 350 which result in alphanumeric display 350 displaying "MYOCARDIAL DISEASE" or, alternatively, an abbreviation thereof, such as "MYO".

In the third position of select display switch 302, both numerical driver 348 and ROM 352 are enabled, so that alphanumeric display 350 provides both a quantitative and a qualitative display of the subject's heart condition.

What is claimed is:
1. An echocardiographic diagnostic apparatus comprising pulse-echo ultrasonic means for insonifying the heart of a subject with successive pulses of ultrasonic wave energy synchronized with the heartbeat of said subject and then detecting echoes of said insonified heart of said subject, said detected echoes including those which when displayed on a cathode-ray-tube display appear as an M-wave, said M-wave having a waveform shape specifically determined by both the movement of said subject's heart as a whole and by the movement of the mitral valve within said subject's heart, said specifically-determined waveform of said M-wave including a first-occurring peak followed, in turn, by a valley and then by a second-occurring peak smaller in amplitude than said first-occurring peak; the combination therewith of an A-wave quantification indicator coupled to said pulse-echo ultrasonic means for measuring the difference in amplitude between said first and second peaks of said M-wave detected echoes and selectively deriving, in accordance with the value of said measured difference, an indication in a form that distinguishes subjects suffering from one of myocardial disease and hyperkinetic syndrome from normal subjects.

2. The apparatus defined in claim 1,
wherein said pulse-echo ultrasonic means comprises adjustable time-delay gating means including a range gate adjustable to be open for a first time interval which includes the time of occurrence of said entire M-wave, an E gate adjustable to be open for a second time interval which includes said first peak but excludes said valley and said second peak of said M-wave, and an A gate adjustable to be open for a third time interval which includes said second peak but excludes said first peak and said valley of said M-wave, and wherein said indicator comprises a gated peak-detector and hold circuit including a storage capacitance, a reversible counter, an analog-to-digital converter coupled between said gated peak-detector and hold circuit and said counter to apply a count input to said counter in accordance with the magnitude of any signal stored in said capacitance, control means coupled to said reversible counter for effecting an UP count in response to the occurrence of said E gate and for effecting a DOWN count in response to the occurrence of said A gate, means for charging said storage capacitance only during said second time interval and during said third time interval and discharging said storage capacitance at the end of said second time interval and at the end of said third time interval, whereby the certain count registered in said reversible counter at the end of a predetermined integral number of one or more complete UP and DOWN cycles thereof is proportional to the difference between said first and second peaks, and output means responsive to said certain count for producing said display indication.

3. The apparatus defined in claim 2,
wherein said output means includes a latch coupled to said reversible counter for storing said certain count, an alphanumeric display and means for controlling said alphanumeric display in accordance the count in said latch.

4. The apparatus defined in claim 3, further including means for resetting said reversible counter after said certain count is registered in said latch.

5. The apparatus defined in claim 4, wherein said means for controlling said alphanumeric display includes a numerical driver to effect the quantitative display of said certain count.

6. The apparatus defined in claim 5, wherein said means for controlling said alphanumeric display includes a read-only-memory for translating said certain count to a certain one of a plurality of different given alphanumeric words of qualitative diagnostic significance in accordance with the value of said certain count to effect the display of said certain one of said given words.

* * * * *

UNITED STATES PATENT AND TRADEMARK OFFICE
CERTIFICATE OF CORRECTION

PATENT NO. : 4,233,989

DATED : November 18, 1980

INVENTOR(S) : Simon Larach et al.

It is certified that error appears in the above—identified patent and that said Letters Patent is hereby corrected as shown below:

Column 5, lines 67 & 68, "ali-phnumeric" should be ---alphanumeric---;

Column 6, line 25, "work" should be ---word---;

Signed and Sealed this

Sixteenth Day of June 1981

[SEAL]

Attest:

RENE D. TEGTMEYER

Attesting Officer — Acting Commissioner of Patents and Trademarks